United States Patent [19]

Cheminal et al.

[11] Patent Number: 5,354,928
[45] Date of Patent: Oct. 11, 1994

[54] PROCESS FOR THE MANUFACTURE OF 1,1,1,2-TETRAFLUOROCHLOROETHANE AND OF PENTAFLUOROETHANE

[75] Inventors: Bernard Cheminal, Brignais; Eric Lacroix, Lyon; Andre Lantz, Vernaison, all of France

[73] Assignee: Societe Atochem, Puteaux, France

[21] Appl. No.: 65,422

[22] Filed: May 24, 1993

Related U.S. Application Data

[63] Continuation of Ser. No. 696,791, May 7, 1991, abandoned.

[30] Foreign Application Priority Data

May 11, 1990 [FR] France .................... 90 05908

[51] Int. Cl.$^5$ ............................................ C07C 17/08
[52] U.S. Cl. ..................... 570/169; 570/134; 570/137; 570/165
[58] Field of Search ............ 570/134, 135, 136, 137, 570/164, 165, 166, 167, 168, 169

[56] References Cited

U.S. PATENT DOCUMENTS

| | | | |
|---|---|---|---|
| 2,110,369 | 3/1938 | Leicester | 570/168 |
| 3,632,834 | 1/1972 | Christoph, Jr. | 570/168 |
| 4,129,603 | 12/1978 | Bell | 570/169 |
| 4,766,260 | 8/1988 | Manzer et al. | 570/168 |
| 4,843,181 | 6/1989 | Gumprecht et al. | 570/169 |

FOREIGN PATENT DOCUMENTS

| | | |
|---|---|---|
| 313061 | 4/1989 | European Pat. Off. . |
| 349298 | 3/1990 | European Pat. Off. . |
| 1568614 | 3/1970 | Fed. Rep. of Germany . |
| 745818 | 3/1956 | United Kingdom ........ 570/166 |
| 1206909 | 9/1970 | United Kingdom . |

OTHER PUBLICATIONS

Patent Abstracts of Japan, vol. 9, No. 91 (C-277) (1814) Apr. 19, 1985 59-225131(A).
Patent Abstracts of Japan, vol. 5, No. 75 (C-55) (747) May 19, 1981 56-24050(A).
European Search Report dated Jan. 30, 1991.

*Primary Examiner*—Johann Richter
*Assistant Examiner*—Michael B. Hydorn
*Attorney, Agent, or Firm*—Morgan & Finnegan

[57] ABSTRACT

The invention relates to a process for the manufacture of 1,1,1,2-tetrafluorochloroethane and of pentafluoroethane.

The process which consists of gas phase catalytic fluorination of at least one pentahaloethane of formula $C_2HX_{2-n}F_{3+n}$ in which X denotes a chlorine or bromine atom and n the number 0 or 1, by hydrofluoric acid, is characterized in that a catalyst is employed consisting of a catalytic quantity of chromium in an oxidation state equal to or greater than 3 and of an activated charcoal as support.

The selectivity for 1,1,1,2-tetrafluorochloroethane and pentafluoroethane reaches approximately 95% and even more.

16 Claims, No Drawings

PROCESS FOR THE MANUFACTURE OF 1,1,1,2-TETRAFLUOROCHLOROETHANE AND OF PENTAFLUOROETHANE

This is a continuation of co-pending application Ser. No. 07/696,791, filed on May 7, 1991, now abandoned.

FIELD OF THE INVENTION

The present invention relates to a continuous process for the manufacture of 1,1,1,2-tetrafluorochloroethane (F124) and of pentafluoroethane (F125) and its subject is more particularly the manufacture of these two compounds by gas phase fluorination of 1,1,1-trifluoro-dichloroethane (F123) by hydrofluoric acid in the presence of a catalyst.

BACKGROUND OF THE INVENTION

Because the compounds F124 and F125 can be employed as substitutes for perchlorofluorocarbons (CFC) in the field of aerosols (propellant agents) and in that of refrigeration, efficient processes for their industrial production are being investigated at present.

U.S. Pat. No. 4,766,260 describes a process for the synthesis of the compounds F123 and F124 by gas phase hydrofluorination of perhalogenated olefins, the objective being to minimize the formation of F125. Example 13 (column 6) describes the fluorination of tetrachloroethylene with a $CrCl_3/Al_2O_3$ catalyst; despite a temperature of 350° C., a long contact time (60 seconds) and a high $HF/C_2Cl_4$ molar ratio (6/1), selectivities for F124 and F125 are low (33.3% and 7.2% respectively).

The use of a chromium(III)-based catalyst ($CrCl_3$) supported on charcoal for the gas phase catalytic fluorination of halogenated olefins forms the subject of Japanese patent application published under No. 48-72,105/73 in which Example 4 describes the fluorination of tetrachloroethylene. Here too, despite a reaction temperature of 400° C. and a high $HF/C_2Cl_4$ molar ratio (5/1), the composition of the products formed is limited to F121 ($CHCl_2-CFCl_2$:6.8%), to F122 ($CHCl_2-CClF_2$:10.5%) and to F123 (82.7%).

U.S. Pat. No. 3,258,500 describes the use of bulk or alumina-supported chromium for gas phase catalytic fluorination reactions. In particular, Example 17 (column 14) describes the fluorination of tetrachloroethylene. At 400° C. with an $HF/C_2Cl_4$ molar ratio of 6.2/1, the selectivity for F123+F124+F125 is low (47.7%); a decrease in the reaction temperature (300° C.) improves this selectivity (79.7%), but the distribution is then shifted towards less-fluorinated products (F123 and F124).

European patent application no. 349,298 describes the synthesis of the compounds F123 and F124 from pentahaloethanes by gas phase catalytic fluorination over a catalyst composed of a metal chosen from chromium, cobalt, nickel and manganese and deposited on alumina. This document places the emphasis, on the one hand, on the extensive activation of the catalyst with hydrofluoric acid (at least 90% of the support in the form of $AlF_3$ after activation) and, on the other hand, on the minimized formation of F125 during the reaction. Thus, in Example 6, which describes the fluorination of F122 at 350° C. and with a long contact time (30 seconds), the selectivity for F125 is only 1.1% and the cumulative selectivity (F123+F124+F125) is only 71.5%. In Example 5, which describes the gas phase fluorination of F123 over a $NiCl_2/Al_2O_3$ catalyst at 400° C., with a contact time of 30 seconds and an HF/F123 molar ratio of 4, the selectivity for F125 is only 7.5%.

A process for producing fluorinated aliphatic hydrocarbons, based on the gas phase fluorination with hydrofluoric acid of halogenated aliphatic hydrocarbons containing at least one halogen atom other than fluorine, forms the subject of U.S. Pat. No. 3,755,477, where the catalyst is a bulk chromium oxide treated with steam before calcination and activation with hydrofluoric acid. Example 25 employs such a catalyst for the fluorination of F123 at 390° C. with a high HF/F123 molar ratio (9.5/1). The selectivities for F125 and F124 are 67 and 21% respectively, but a selectivity of 2.5% for chloropentafluoroethane (F115), which cannot be recycled is also observed.

From the examination of the state-of-the-art it appears difficult to synthesize the two desired compounds (F124 and F125) with a good selectivity and a high production efficiency by direct fluorination of tetrachloroethylene or of F122. When starting with tetrachloroethylene and despite long contact times and high temperatures and molar ratios it appears difficult to obtain F124 and more especially F125 in high yields. The synthesis of both these compounds is easier from F122, but a selectivity problem (extensive formation of by-products) is confronted in this case.

As for U.S. Pat. No. 3,755,477, this shows that when starting from F123 the synthesis of F125 requires a high molar ratio (9.5) and a high temperature (390° C.), the association of which results in a significant undesirable formation of F115.

In view of the interest in compounds F124 and F125 as CFC substitutes, their industrial manufacture requires a particularly efficient process, that is to say one making it possible to obtain:

a very high selectivity for F124 +F125 a high production efficiency for F124 and/or F125 a high flexibility in order to direct the manufacture at will towards the preponderant production of F124 or towards that of F125, while minimizing the by-product formation.

DESCRIPTION OF THE INVENTION

Such a process has now been found, and consists in fluorination in gaseous phase at least one pentahaloethane of formula $C_2HX_{2-n}F_{3+n}$ in which X denotes a chlorine or bromine atom and n the number 0 or 1, by means of hydrofluoric acid over a catalyst consisting of a catalytic quantity of chromium in an oxidation state equal to or higher than 3 and of an activated charcoal as support. In fact, a catalyst of this kind makes it possible to obtain a selectivity for F124+F125 of approximately 95% or more, and at the same time to minimize the formation of F124a (1-chloro-1,1,2,2-tetrafluoroethane).

The starting pentahaloethane is preferably F123, by itself or mixed with F123a (1,2-dichloro-1,1,2-trifluoroethane). However, for the preferential manufacture of F125 the starting compound employed may also be F124 itself, its isomer F124a, F123b (1,1-dichloro-1,2,2-trifluoroethane) or a mixture of these compounds. Furthermore, certain reaction products ( for example F122, $C_2Cl_4$, $CFCl=CCl_2$, $CF_2=CCl_2$ and F124a) can be recycled to the fluorination reactor. It would therefore not constitute a departure from the scope of the present invention to feed the reactor with a mixture containing, on a molar basis, at least 50% of F123 and/or F124, from 0 to 5% of underfluorinated compounds and from 0 to 50% of F123a, F123b and/or F124a.

Although it is preferred to start with chloro pentahaloethanes $C_2HCl_{2-n}F_{3+n}$, the process according to the invention can be applied to their bromo homologues such as, for example, 1-bromo-1-chloro-2,2,2-trifluoroethane ($CF_3CHBrCl$), 1,1-dibromo-2,2,2-trifluoroethane ($CF_3CHBr_2$), 1-bromo-2-chloro-1,1,2-trifluoroethane ($CF_2BrCHClF$) or 1,1-dibromo-1,2,2-trifluoroethane ($CFBr_2CHF_2$).

The catalyst to be employed in accordance with the present invention can be prepared by impregnating an activated charcoal with a solution of a chromium-based compound. The chromium-based active species may be in the form of oxides, hydroxides, halides (with the exception of iodine), oxyhalides, nitrates, sulphates or other chromium compounds, the preferred compound being chromium(III) oxide.

The active species content of the catalyst, expressed as chromium metal, may range from 0.1 to 50% by weight and is preferably between 1 and 20%.

A more particularly preferred catalyst is a chromium oxide-based catalyst on an activated charcoal exhibiting a high total specific surface area (higher than 800 m$^2$/g). Catalysts of this type can be obtained, as indicated in European Patent No. 55,659, by impregnating activated charcoal with an aqueous solution of chromium trioxide, followed by drying at a temperature of between 100° and 300° C., preferably between approximately 150° and 200° C. In the final catalyst most of the chromium trioxide is reduced to the sesquioxide state $Cr_2O_3$ by the activated charcoal itself.

The activation of the dry catalyst is specific and must be adapted to the catalytic entity deposited onto the activated charcoal support. As a general rule, inactivated catalysts containing no oxygen must be fluorinated in the presence of a source of oxygen (for example air) or must undergo a heat treatment, also in the presence of a source of oxygen. On the other hand, a catalyst whose catalytic entity is a chromium oxide can be fluorinated directly, optionally after rigorous drying under nitrogen (approximately 400° C.) with hydrofluoric acid, diluted with nitrogen or undiluted. To preserve the catalyst activity it is advantageous to control the exothermicity of its activation and to avoid heating it to an excessively high temperature (600°–700° C.). It is therefore recommended to begin the fluorination at low temperature and then, after the exothermicity "waves", to increase the temperature gradually to reach 350° to 450° C. at the end of activation.

In accordance with the process according to the invention, the fluorination reaction of pentahaloethane with HF may be conducted at a temperature ranging from 250° to 470° C. and, more particularly, at a temperature of between 280° and 410° C. However, if it is desired to direct the reaction towards the preferential synthesis of F124, it will be more appropriate to work at a temperature situated in the lower part (300°–330° C.) of the abovementioned range; conversely, a higher temperature promotes the synthesis of F125.

The contact time in the case of the reaction according to the invention may be between 3 and 100 seconds and, more particularly, between 5 and 30 seconds. However, in order to obtain a satisfactory compromise between the degree of conversion of F123 and the high production efficiencies for F124 and/or F125, the best range is from 7 to 15 seconds.

The HF/pentahaloethane molar ratio may range from 1/1 to 20/1 and preferably from 2/1 to 9/1. Here too, the degree of conversion of F123 and the distribution of the products which are formed vary with the chosen molar ratio, an increase in the molar ratio resulting in an improvement in the degree of conversion of F123 and in a shift of the products formed towards more highly fluorinated compounds (F125). It should be noted, however, that a low molar ratio (lower than 2) increases the formation of products which cannot be recycled (perhaloethanes and tetrahaloethanes).

The fluorination reaction according to the invention can be conducted in a gas phase fluorination reactor in a stationary bed or in a fluid bed. The materials of construction employed for the plant must be compatible with the presence of hydrogen acids such as HCl and HF; they must be chosen from "Hastelloy" or "Inconel" which are resistant to the corrosive media containing these hydrogen acids.

The fluorination reaction according to the invention may be conducted at atmospheric pressure or at a pressure higher than the latter. For practical reasons the operation would be generally carried out in a region ranging from 0 to 25 bars gauge.

The application of the process according to the invention makes it possible to obtain the two desired pentahaloethanes F124 and F125 with an excellent selectivity (equal to or higher than approximately 95%), the proportion of isomers and of products which cannot be recycled (perhaloethanes and tetrahaloethanes) being very low. The process according to the invention also exhibits a very high flexibility; as shown by the following examples, the F124/F125 molar ratio in the product obtained can vary from 10/1 to 1/10 depending on the operating conditions. Furthermore, the possibility of operating with low molar ratios and short contact times allows a good production efficiency to be obtained, while giving a satisfactory degree of conversion of F123.

The underfluorinated products formed (F122:0–0.2% and F1111:0.1–1.2%) can be isolated or recycled with the unconverted F123 and F123a. If desired, the compounds F124 and F124a can also be recycled to the reactor to increase the production efficiency of F125.

EXAMPLES

In the following examples, which illustrate the invention without limiting it, the percentages shown are molar percentages and the hydrofluoric acid employed is a commercial product containing only traces of water.

EXAMPLE 1: PREPARATION OF THE CrIII/CHARCOAL CATALYST 250 ml (103 g) of a vegetable activated charcoal pre-dried at 150° C. and exhibiting the following characteristics:

| | |
|---|---|
| apparent relative density | 0.41 |
| particle size | 0.8 mm extrudates |
| BET surface area | 922 m$^2$/g |
| surface area of the 50–250 Å pores | 20.4 m$^2$/g |
| surface area of the 250–320 Å pores | 3.2 m$^2$/g | are impregnated with an aqueous solution of 56 g (0.56 moles) of chromium trioxide in 65 g of water.

The activated charcoal absorbs all the aqueous solution. The catalyst is then dried in a fluidized bed using air at 150° C.

Analysis of the dry catalyst shows that most of the chromium is in the trivalent state.

EXAMPLES 2 TO 8: FLUORINATION OF F123

The F123 employed as starting organic reactant is a crude product consisting essentially of F123 (96.1%), the other compounds being F123a (3.6%), F123b (less than 0.1%) and F113 (approximately 0.1%).

The reactor employed is a 250-ml Inconel tube heated by means of a fluidized alumina bath.

100 ml of the catalyst obtained as described in Example 1 are charged into this rector. The catalyst is first of all dried under a stream of air (2 l/h) at 120° C. for 5 hours and then hydrofluoric acid containing air is added gradually at this same temperature over a period of 3 hours (one mole of HF introduced over 3 hours). After this first low-temperature activation stage the catalyst is heated under a nitrogen stream (1 l/h) up to 400° C. When this temperature is reached the nitrogen is replaced gradually with hydrofluoric acid to complete the activation with pure HF (0.5 mole/hour) for 8 hours at 400° C.

The temperature of the activated catalyst is then adjusted, under nitrogen purging (0.5 l/h), to the value chosen for the envisaged fluorination reaction. The nitrogen stream is then replaced with a stream of HF and of crude F123, these reactants having been premixed and heated to the reaction temperature in an Inconel preheater. The proportions of HF and F123 and the feed rate are adjusted as a function of the chosen values for the HF/F123 molar ratio and the contact time.

After washing with water to remove the hydrogen acids and drying over calcium chloride, the products leaving the reactor are analyzed in line by gas phase chromatography. The instrument employed is a DELSI IGC 11 chromatograph fitted with a tungsten 200 mA filament and a column 5 m in length and 3.175 mm in diameter, packed with a mixture of UCON LB 550 X (polypropylene glycol) at a concentration of 25% on SPHEROSIL XOA 200 (porous silica support). The carrier gas is helium (20 ml/min) and the analysis temperature is kept constant at 100° C.

The following table collates the operating conditions and the results obtained in various operations carried out at atmospheric pressure on two different batches of the same catalyst: the first batch in the case of operations 2 to 5 and the second in the case of operations 6 to 8. The age of the catalyst corresponds to its total operating period since being put into service, that is to say since the original introduction of a mixture of HF+crude F123 (operations 2 and 6 respectively).

| EXAMPLES | 2 | 3 | 4 | 5 | 6 | 7 | 8 |
|---|---|---|---|---|---|---|---|
| OPERATING CONDITIONS | | | | | | | |
| Temperature (°C.) | 350 | 350 | 300 | 330 | 340 | 340 | 340 |
| HF/F123 molar ratio | 5 | 2.9 | 3 | 2 | 3.3 | 4.3 | 3.3 |
| Contact time (seconds) | 9.7 | 9.7 | 11.2 | 9.7 | 9.9 | 9.9 | 10.3 |
| Catalyst age (hours) | 59 | 65 | 69 | 87 | 60 | 84 | 210 |
| RESULTS | | | | | | | |
| Degree of conversion of F123 (%) | 90.4 | 83.4 | 49.2 | 66.8 | 78.8 | 83.5 | 78.4 |
| Selectivity (%) for: | | | | | | | |
| F124 ($CF_3CHFCl$) | 17.7 | 22.6 | 87.8 | 43 | 25.9 | 24.9 | 27 |
| F125 ($CF_3CHF_2$) | 78.8 | 71.6 | 10 | 52.4 | 70.1 | 72 | 69 |
| F122 ($CF_2ClCHCl_2$) | 0 | 0.05 | 0 | 0.1 | 0.05 | 0 | 0 |
| F123a ($CF_2ClCHFCl$) | 0 | 0 | 0 | 0 | 0 | 0 | 0 |
| F124a ($CF_2ClCHF_2$) | 0.2 | 0.3 | 0.8 | 0.2 | 0.3 | 0.2 | 0.3 |
| F1111 ($Cl_2C{=}CFCl$) | 0.1 | 0.2 | 0.1 | 0.1 | 0.3 | 0.1 | 0.2 |
| F114 + F114a ($C_2F_4Cl_2$) | 1.7 | 2.1 | 0.3 | 1.5 | 1.3 | 1.1 | 1 |
| F115 ($C_2ClF_5$) | 0.4 | 0.5 | 0.1 | 0.4 | 0.3 | 0.3 | 0.5 |
| F133a ($CF_3CH_2Cl$) | 0.9 | 1.3 | 0.6 | 1.3 | 1.1 | 1 | 0.9 |
| F1110 ($Cl_2C{=}CCl_2$) | 0 | 1.2 | 0.5 | 0.6 | 0.5 | 0.1 | 0.4 |

Comparison of Examples 6 and 8 shows that the catalytic activity is maintained perfectly with time.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the selective preparation of 1,1,1,2-tetrafluorochloroethane or 1,1,1,2-tetrafluorobromoethane, and of pentafluoroethane, comprising fluorinating under catalytic gas phase conditions at least one pentahaloethane of formula $C_2HX_{2-n}F_{3+n}$ in which X denotes a chlorine or bromine atom and n the number 0 or 1, by means of hydrofluoric acid, wherein the catalyst employed consists of a catalytic quantity of chromium in an oxidation state equal to or greater than 3 and an activated charcoal as support whereby formation of tetrahaloethanes and perhaloethanes is minimized.

2. Process according to claim 1, wherein selectivity for 1,1,1,2-tetrafluorochloroethane and pentafluoroethane is greater than about 95%.

3. Process according to claim 1, comprising depositing the chromium onto the activated charcoal in the form of an oxide; hydroxide; nitrate.; sulphate; oxyhalide; or halide selected from the group consisting of fluoride, chloride, bromide, and astatide.

4. Process according to claim 3, wherein chromium is in the form of chromium(III) oxide.

5. Process according to claim 1, wherein the active species content of the catalyst, expressed as chromium metal, is between 0.1 and 50% by weight.

6. Process according to claim 5, wherein the active species content of catalyst is between 1 and 20%.

7. Process according to claim 1, wherein the catalyst has a total specific surface area greater than about 800 m²/g.

8. Process according to claim 1, comprising contacting the hydrofluoric acid and said pentahaloethane in an HF/pentahaloethane molar ratio of between 1/1 and 20/1 for a time of between 3 and 100 seconds and at a temperature of between 250° and 470° C.

9. Process according to claim 8 wherein the molar ratio is between 2/1 and 9/1, the contact time is between 5 and 30 seconds, and the temperature is between 280° and 410° C.

10. Process according to claim 9, wherein the contact time is between 7 and 15 seconds.

11. Process according to claim 1, wherein the pressure is from 0 to 25 bars gauge.

12. Process according to claim 11, wherein the pressure is atmospheric pressure.

13. Process according to claim 1, wherein the starting pentahaloethane is selected from the group consisting of 1,1,1-trifluoro-dichloroethane, and 1,1,1,2-tetrafluorochloroethane, or a mixture thereof.

14. Process according to claim 1, wherein the starting material is a mixture containing, on a molar basis, at least 50% of a component selected from the group consisting of 1,1,1-trifluorodichloroethane, and 1,1,1,2-tetrafluorochloroethane, or a mixture thereof; from 0 to 5% of recycled underfluorinated compounds; and from 0 to 50% of a component selected from the group consisting of 1,2-dichloro-1,1,2-trifluoroethane, 1,1-dichloro-1,2,2-trifluoroethane, and 1-chloro-1,1,2,2-tetrafluoroethane, or a mixture thereof.

15. Process according to claim 1, wherein the starting pentahaloethane is selected from the group consisting of 1,1,1-trifluorodichloroethane, and 1,2-dichloro-1,1,2-trifluoroethane, or a mixture thereof.

16. Process according to claim 1, wherein the starting pentahaloethane is selected from the group consisting of 1,1,1,2-tetrafluorochloroethane, and 1-chloro-1,1,2,2-tetrafluoroethane, and 1,1-dichloro-1,2,2-trifluoroethane, or a mixture thereof.

* * * * *